US00PP25507P3

(12) United States Plant Patent
Higaki

(10) Patent No.: US PP25,507 P3
(45) Date of Patent: May 5, 2015

(54) *HYDRANGEA* PLANT NAMED 'BC8.3'

(50) Latin Name: ***Hydrangea macrophylla* (Thunb.)**
Varietal Denomination: BC8.3

(71) Applicant: Harrison M. Higaki, San Mateo, CA (US)

(72) Inventor: Harrison M. Higaki, San Mateo, CA (US)

(73) Assignee: Bay City Flower Company, Half Moon Bay, CA (US)

( * ) Notice: Subject to any disclaimer, the term of this patent is extended or adjusted under 35 U.S.C. 154(b) by 0 days.

(21) Appl. No.: 13/986,180

(22) Filed: Apr. 8, 2013

(65) Prior Publication Data

US 2014/0304865 P1 Oct. 9, 2014

(51) Int. Cl.
*A01H 5/00* (2006.01)

(52) U.S. Cl.
USPC ..... Plt./250

(58) Field of Classification Search
CPC ..... A01H 5/00
USPC ..... Plt./250
See application file for complete search history.

*Primary Examiner* — June Hwu
*Assistant Examiner* — Keith O. Robinson
(74) *Attorney, Agent, or Firm* — James R. Cypher; Charles R. Cypher

(57) ABSTRACT

A new and distinct cultivar of *Hydrangea macrophylla* (Thunb.) named 'BC8.3' originated as a controlled cross between varieties. The cultivar 'BC8.3' can be blue or red depending on the acidity of the soil and the presence of aluminum. The variety 'BC8.3' has compact, attractive inflorescences with large sepalous florets that do not completely hide the non-sepalous florets at the center of the cyme, attractive sepal pigmentation, and stems that branch easily and are relatively strong. When grown without aluminum, the upper sides of the sepals of the sepalous florets are primarily R.H.S. 73 A (red-purple group) at the center of the floret and the sepals are R.H.S 56 A (red group) at their periphery.

3 Drawing Sheets

Botanical classification: *Hydrangea macrophylla* (Thunb.) 'BC8.3'.

Variety denomination: 'BC8.3'.

BACKGROUND OF THE INVENTION

This invention relates to a new and distinct cultivar of the Saxifragaceae family. The botanical name of the plant is *Hydrangea macrophylla* (Thunb.) 'BC8.3'.

The new cultivar originated as a seedling from a controlled cross between the unpatented, commercial variety known as 'Nizza' (seed parent) to the inventor, and an unpatented, commercial variety known as 'Messalina' (pollen parent) to the inventor. The variety 'BC8.3' is similar to the pollen parent 'Messalina' which also has relatively large sepalous florets that ring and almost hide all of the non-sepalous florets in the center of the panicle. In comparison, the seed parent 'Nizza' has fewer sepalous florets than either 'BC8.3' or 'Messalina'. Both 'Messalina' and 'Nizza' differ from the new variety 'BC8.3' in that they have corrugated sepals and florets that are cup-shaped at maturity, while the sepals of the new variety 'BC8.3' are flat and spreading.

The variety 'BC8.3' has compact, attractive inflorescences with relatively large sepalous florets that ring and almost hide all of the non-sepalous florets in the center of the panicle, attractive sepal pigmentation, grows well under commercial conditions, and stems that branch easily and are relatively strong. This combination of characteristics makes the plant ideal for commercial production as an ornamental potted plant. Below is a table comparing the new variety to similar varieties. The new variety was grown alongside the commercial variety known as 'Venedig' (grown as a pink variety) to the inventor, which may be an alias for the patented variety 'Venice Raven'—U.S. Plant Pat. No. 10,928, as a control.

TABLE 1

| | Currently Patent Pending Variety 'BC8.3' (13/986,180) | Currently Patent Pending Variety BCHY-07.013'- (13/986,181) |
|---|---|---|
| Leaf size | 10 cm × 16 cm | 9 cm × 16.5 cm |
| Plant height | 15" in 6" pot. | 18" in 6" pot. |
| Stem strength | Stems are relatively strong. | Stems are relatively strong. |
| Sepal Pigmentation | Upper side of sepals is R.H.S. 73 A (red-purple group) in center and margins of sepals are R.H.S. 56 A (red group). | Upper side of sepals is R.H.S. 61 B (red-purple group); Under side of sepals is R.H.S. 70 C (red-purple group). |
| Sepalous Floret Size | 70 mm | 65 mm |

| | Currently Patent Pending Variety New Variety 'BC7.12' (13/986,047) | Commerical variety 'Venedig' which may be U.S. Plant Pat. No. 10,928 'Venice Raven' Grown without aluminum |
|---|---|---|
| Leaf size | 9 cm × 16.5 cm | Unknown |
| Plant height | 17" in 6" pot. | 12" in 6" pot - observed controls grown alongside new variety. |
| Stem strength | Stems are strong. | Strong - observed controls grown alongside new variety |
| Sepal Pigmentation | Upper side of sepals is R.H.S. 67 A (red-purple group); Under side of sepals | Upper side of sepals is R.H.S. 74 C (red-purple group). Under side |

TABLE 1-continued

| | | |
|---|---|---|
| | is R.H.S. 68 A (red-purple group). | of sepals is R.H.S. 75 B (purple group) observed controls grown alongside new variety. |
| Sepalous Floret Size | 60 mm | 50 mm - observed controls grown alongside new variety |

The new cultivar 'BC8.3' has been successfully asexually reproduced under controlled environmental conditions at a nursery in Half Moon Bay, Calif. under the direction of the inventor with its distinguishing characteristics remaining stable.

Asexual reproduction was first accomplished when vegetative cuttings were taken from the initially selected plant. Examination of asexually reproduced, successive generations grown in Half Moon Bay, Calif. show that the combination of characteristics as herein disclosed for 'BC8.3' remains firmly fixed.

DESCRIPTION OF THE DRAWINGS

The accompanying drawings consist of color photographs that show the typical plant form, including the inflorescence, foliage, and sepals, although color representations are not accurate and thus references in the specification should be used for comparison and characterization of the new variety.

DESCRIPTION OF THE NEW PLANT

Figure 1:
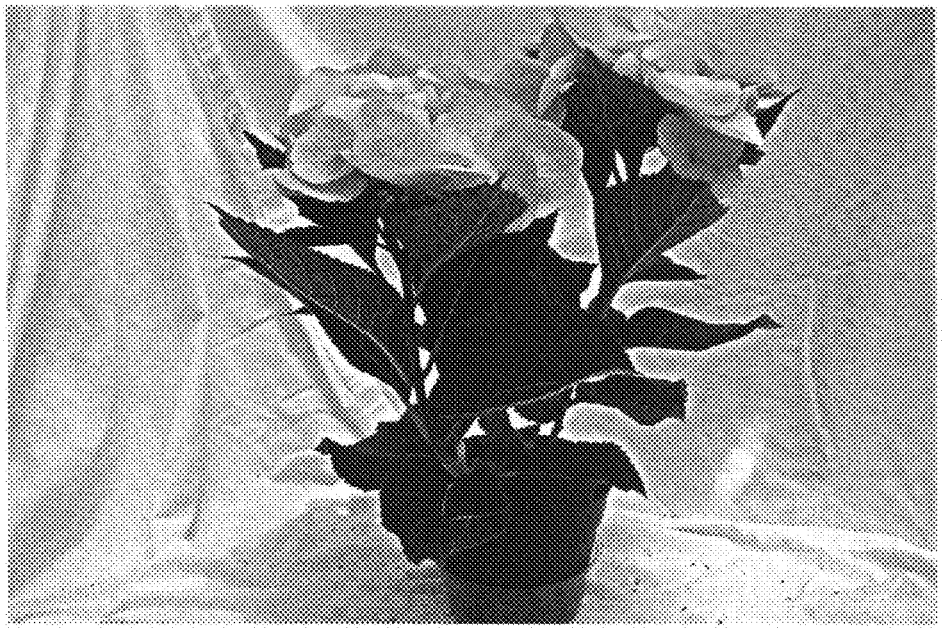
FIG. 1 is a view of the entire plant showing its form, growth habit, dark green foliage, inflorescence, and the color of its sepals.
Figure 2:
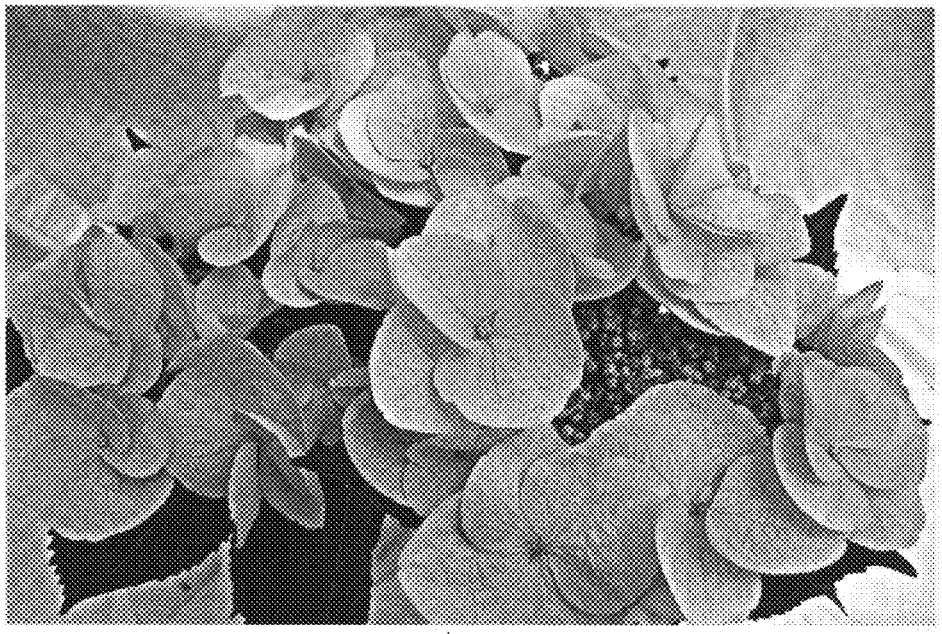
FIG. 2 is a top view of the plant showing its inflorescences and the color of the sepals.
Figure 3:
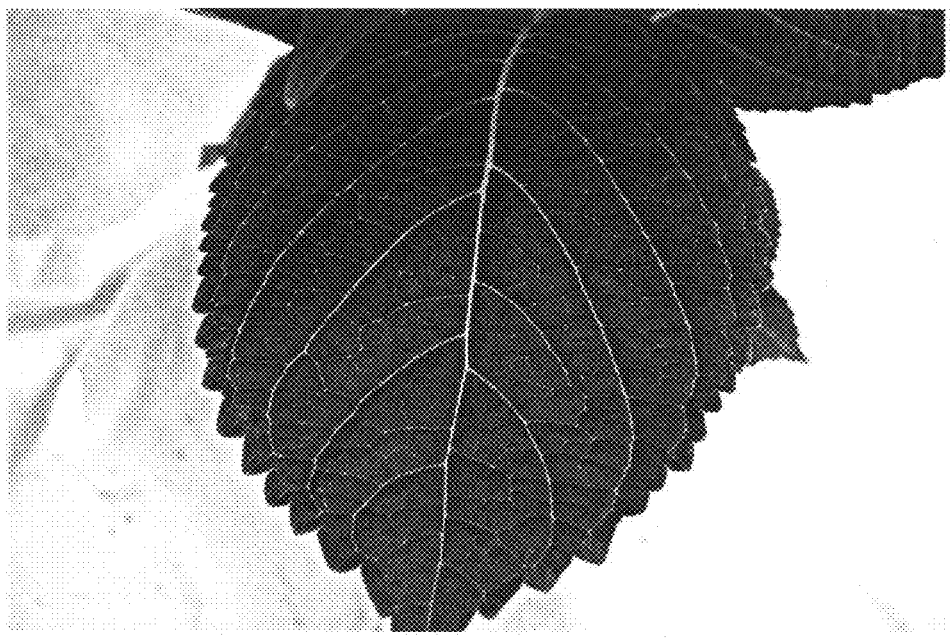
FIG. 3 is a close-up of the adaxial surface of a mature leaf.
Figure 4:
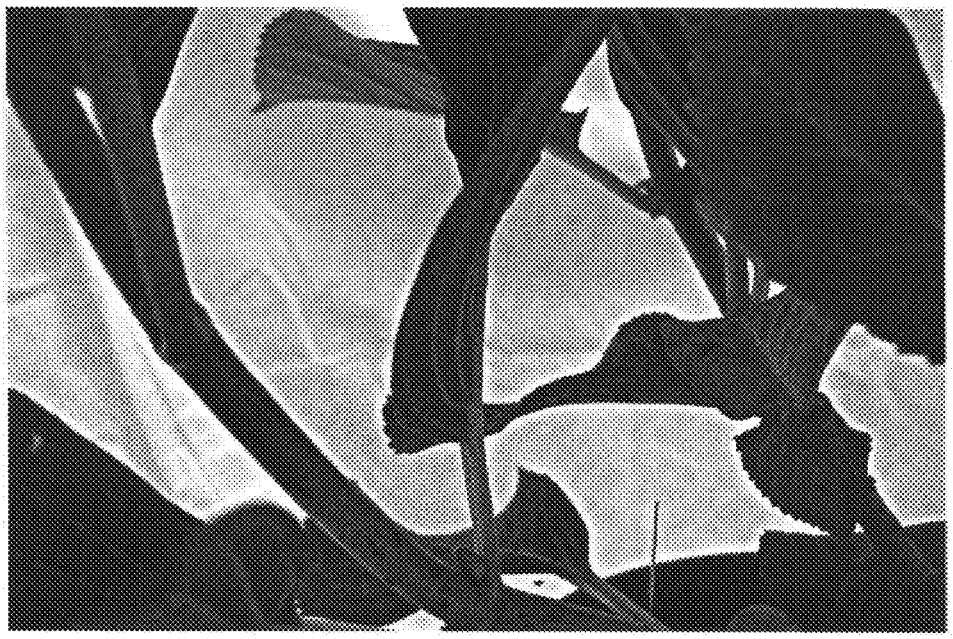
FIG. 4 is a close-up view of the base of the stem.
Figure 5:
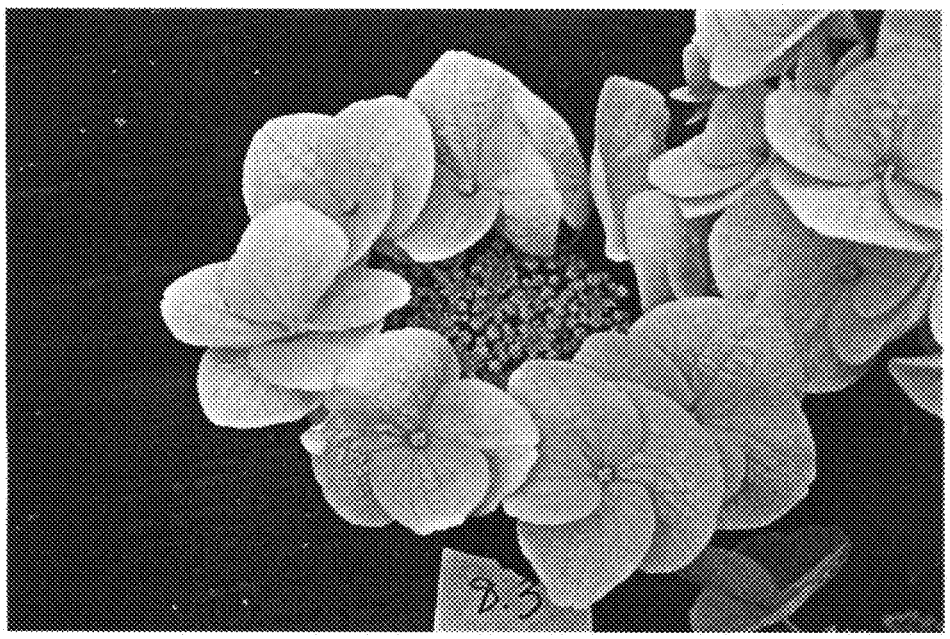
FIG. 5 is a close-up view of the upper side of a panicle of the new variety.
Figure 6:
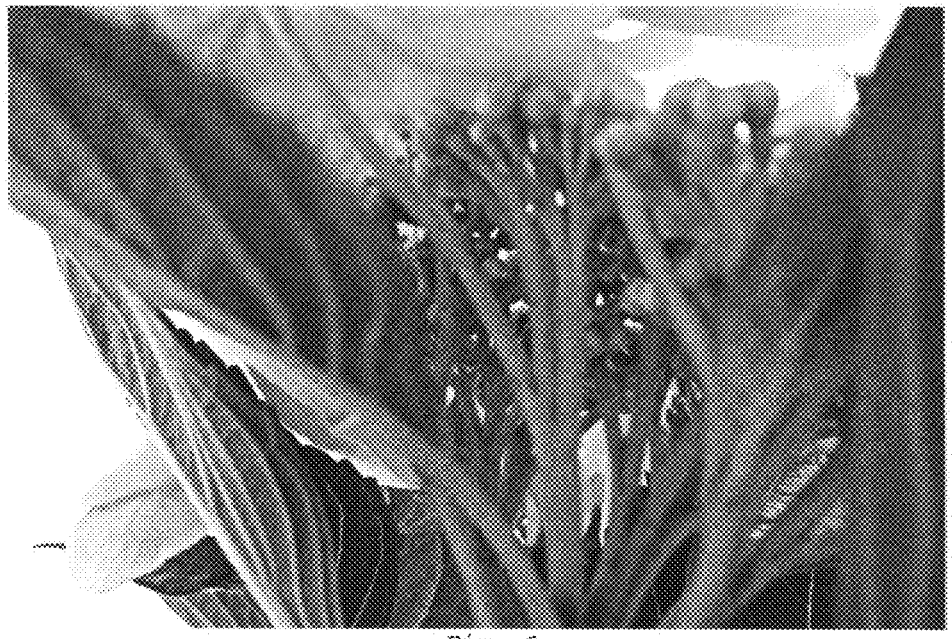
FIG. 6 is a close-up view of the center of a panicle of the new variety.

The plants shown in the figures are approximately 1 years old. The plant started out as cuttings, taken from the stem of a grown plant. The cuttings were placed in a pot and the soil was periodically fertilized. The plant was pinched early to promote lateral branches.

'BC8.3' has not been observed under all possible environmental conditions. The phenotype may vary significantly with variations in environment such as temperature, light intensity and day length. Color determinations were made with The Royal Horticultural Society (R.H.S.) Colour Chart, in association with the Flower Council of Holland, located in Lieden.

THE PLANT

Origin: Controlled cross. The new cultivar originated as a seedling from a controlled cross between the commercial variety known to the inventor as 'Nizza', and the commercial variety 'Messalina'.

Form: Upright, compact shrub. A typical plant with a mature inflorescence that is ready for sale is approximately 15" high and has a diameter of 16" when grown in a 6" pot with appropriate soil amendments. Plants typically have 4 to 6 stems with one inflorescence between each stem.

Growth: Upright, vigorous growth habit. Inflorescence is large. The plant branches easily with shoots forming at the base of the plant. Lateral branches are similar in appearance and form to the main stems.

Stems: Lenticels are present. Lenticels are R.H.S. 86 A (violet group) and are 1 to 2 mm long. The surface of young stems is glabrous. Stems become woody as they age. The color of typical young stems and young lateral branches is R.H.S. 144 A (green group). The older portions of the stems are R.H.S. 197 A (grey-green group) Younger portions of the stems are 6 mm in diameter. Older portions of the stems are 1 cm in diameter.

Foliage: Abundant. Leaves are opposite on stem and lateral branches.

*Shape of leaf*.—Elliptic with acute base and apex. Margins are serrate.

*Texture*.—Glabrous, non-glossy; veins dominate on the underside of the leaf and are sunken on the upper leaf surface.

*Color*.—Mature leaves have an upper side that is R.H.S. 147 A (yellow-green group), and an under side that is R.H.S. 138 B (green group). Leaves are pinnately veined. The midvein and veins branching off the midvein are large and prominent on the underside of the leaves. Veins are R.H.S. 144 D (yellow-green group). Other than the different colors of the upper and lower surfaces of the leaves and the contrast in vein color from the upper surface color of the leaves the color of the leaf surfaces are uniform. Leaves are as wide as 10 cm and 16 cm long. Petioles are smooth and 2 to 2.5 cm long and 4 mm wide. Petioles are R.H.S. 144 D (yellow-green group).

BUDS

Form: Globose with 4 to 5 connate, elliptic, smooth petals for both sepalous and non-sepalous buds. Buds in the center of the inflorescence are non-sepalous. The buds surrounding the outside of the inflorescence will develop into sepalous florets. Buds are approximately 1 mm by 1 mm when very young. Buds can be 5 mm in diameter and still unopened. Color of buds is R.H.S. 77 C (red-purple group) when almost ready to open. Buds are R.H.S. 145 D (yellow-green group) when immature.

Aspect: Smooth.

Arrangement: Borne on branched panicles.

INFLORESCENCE

Form: Paniculate. Terminal. As many as 100 individual flowers (both sepalouos and non-sepalous florets) per inflorescence. Both sepalous florets and non-sepalous florets borne on same panicle with many more non-sepalous florets than sepalous florets. Flowers do not produce a fragrance. The peduncle for the inflorescence is strong and upright. Non-sepalous florets in the center of the panicle develop early on cymes and are later somewhat hidden by the sepalous florets. Florets, both sepalous and non-sepalous, have anthers and style. Inflorescences are long-lasting, changing color as they age.

Size of inflorescence: Compact and rather flat. Individual inflorescence size is dependent on the number of florets. A typical inflorescence can grow as large as 8" in diameter, and be 4" high.

Shape: Clusters of numerous small florets; sepalous florets overlap one another. Sepals are persistent.

Appearance: Somewhat showy.

FLORETS

General: The non-sepalous florets at the center of the inflorescence open first. Sepalous and non-sepalous florets are perfect and complete.

*Corolla*.—Generally, for both sepalous and non-sepalous florets the petals fall off as flower matures. Petals are typically 4 mm long and 3 mm wide. Petals are R.H.S. 77 C (red-purple group). Lenticels that are very small are present on pedicels of both sepalous and non-sepalous florets. Lenticels are R.H.S. 59 B (red-purple) group. Pedicel of both sepalous and non-sepalous florets are primarily R.H.S. 68 A (red-purple group) when inflorescence is ready for commercial sale. Pedicels of non-sepalous florets are 6 mm long, and pedicels of sepalous florets are up to 40 mm long.

Stamens: 8 to 10 stamens. Pollen is R.H.S. 158 C (yellow-white group). Plant produces abundant pollen. Filament is R.H.S. 72 A (red-purple group) and 3 mm long. Anther is 1 mm long and is regular and basally attached.

Stigma: Two to three style each ovary, sometimes four. Each style has one stigma. Style is typically 1 mm long. For young inflorescences ready for commercial sale style is R.H.S. 73 A (red-purple group) and stigma is R.H.S. 72 A (red-purple group).

Ovary: Ovary is partially inferior. Ovary is 5 mm in diameter.

Sepalous florets:

*General*.—Veins dominate on the underside of the sepals.

*Number of sepals*.—3 to 5 sepals per floret, with most having 4 sepals.

*Aspect of sepals*.—Smooth and glaucescent.

*Shape of sepals*.—Reniform with acuminate apex. Edges are entire, but with crenation.

*Size of sepals*.—As the florets mature, the sepals enlarge and overlap each other more and more, until, often, there is no space between the sepals when the petals of the florets open. Sepals at maturity are typically 40 mm long and 45 mm wide, with some being as wide as 60 mm. Flowers are typically 7 cm in diameter. The color of the sepals can be blue or red depending on the acidity of the soil and the presence of aluminum. When grown without aluminum in alkaline soils, the upper sides of the sepals near the center of the floret are primarily R.H.S. 73 A (red-purple group) with the margins of the sepals being R.H.S. 56 A (red group). The color of the sepals typically fades near the tips of the sepals.

Fruit: None.

Disease and pest resistance: Unknown.

I claim:

1. A new and distinct *Hydrangea macrophylla* plant named 'BC8.3' substantially as herein shown and described.

* * * * *